(12) United States Patent
Iyengar et al.

(10) Patent No.: US 8,383,785 B2
(45) Date of Patent: Feb. 26, 2013

(54) ANTI-BACTERIAL ACTIVITY OF 9-HYDROXY DERIVATIVES OF 6,11-BICYCLOLIDES

(75) Inventors: Rajesh Iyengar, West Newton, MA (US); Yanchun Wang, Newton, MA (US); Ly Tam Phan, Quincy, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 533 days.

(21) Appl. No.: 12/437,616

(22) Filed: May 8, 2009

(65) Prior Publication Data
US 2009/0281050 A1 Nov. 12, 2009

Related U.S. Application Data

(60) Provisional application No. 61/051,991, filed on May 9, 2008.

(51) Int. Cl.
*C07H 17/08* (2006.01)
*A61K 31/7048* (2006.01)
*C07D 493/08* (2006.01)

(52) U.S. Cl. .............................. 536/7.4; 514/29; 549/270
(58) Field of Classification Search .................. 536/7.4, 536/18.5; 514/29; 549/270
See application file for complete search history.

(56) References Cited

U.S. PATENT DOCUMENTS

| | | | |
|---|---|---|---|
| 4,990,602 A | 2/1991 | Morimoto et al. |
| 5,444,051 A | 8/1995 | Agouridas et al. |
| 5,527,780 A | 6/1996 | Agouridas et al. |
| 5,556,839 A | 9/1996 | Greene et al. |
| 5,631,355 A | 5/1997 | Asaka et al. |
| 5,780,605 A | 7/1998 | Or et al. |
| 5,866,549 A | 2/1999 | Or et al. |
| 5,922,683 A | 7/1999 | Or et al. |
| 6,034,069 A | 3/2000 | Or et al. |
| 6,046,171 A | 4/2000 | Or et al. |
| 6,054,435 A | 4/2000 | Or et al. |
| 6,075,133 A | 6/2000 | Or et al. |
| 6,124,269 A | 9/2000 | Phan et al. |
| 6,274,715 B1 | 8/2001 | Or et al. |
| 6,355,620 B1 | 3/2002 | Ma et al. |
| 6,764,998 B1 | 7/2004 | Wang et al. |
| 6,878,691 B2 | 4/2005 | Or et al. |
| 7,022,679 B2 | 4/2006 | Kim et al. |
| 7,049,417 B2 | 5/2006 | Or et al. |
| 7,064,110 B2 | 6/2006 | Or et al. |
| 7,129,221 B2 | 10/2006 | Or et al. |
| 7,135,573 B2 | 11/2006 | Kim et al. |
| 7,189,704 B2 | 3/2007 | Niu et al. |
| 7,229,972 B2 | 6/2007 | Or et al. |
| 7,265,094 B2 | 9/2007 | Qiu et al. |
| 7,273,853 B2 | 9/2007 | Or et al. |
| 7,384,921 B2 | 6/2008 | Tang et al. |
| 7,384,922 B2 | 6/2008 | Wang et al. |
| 7,414,030 B2 | 8/2008 | Vo et al. |
| 2005/0009761 A1 | 1/2005 | Or |
| 2005/0187169 A1 | 8/2005 | Vo et al. |
| 2006/0252712 A1 | 11/2006 | Wang et al. |
| 2007/0082853 A1 | 4/2007 | Or et al. |
| 2007/0244160 A1 | 10/2007 | Or et al. |
| 2009/0075915 A1 | 3/2009 | Kim et al. |
| 2009/0118506 A1 | 5/2009 | Kim et al. |
| 2009/0264380 A1 | 10/2009 | Kim et al. |
| 2009/0270457 A1 | 10/2009 | Kim et al. |
| 2009/0324577 A1 | 12/2009 | Or et al. |

FOREIGN PATENT DOCUMENTS
WO 2009075923 A2 6/2009

OTHER PUBLICATIONS
Ettmayer et al. J. Med. Chem., 2004, 47(10), p. 2393-2404.*
International Search Report from PCT/US09/43225, dated Aug. 13, 2009.

* cited by examiner

*Primary Examiner* — Shaojia Anna Jiang
*Assistant Examiner* — Jonathan S Lau
(74) *Attorney, Agent, or Firm* — Edgar W. Harlan; Carolyn S. Elmore, Esq.; Elmore Patent Law Group, PC

(57) ABSTRACT

The present invention discloses compounds of formula (I) or pharmaceutically acceptable salts, esters, or prodrugs thereof:

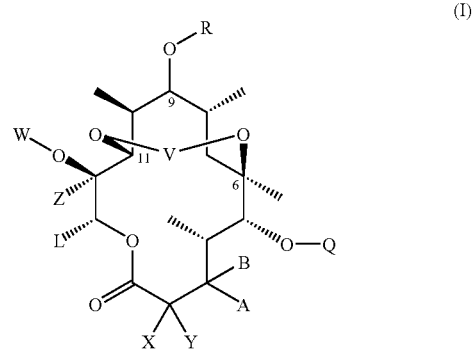

(I)

which exhibit superior antibacterial properties, particularly against *Haemophilus influenzae*. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

9 Claims, No Drawings

ANTI-BACTERIAL ACTIVITY OF 9-HYDROXY DERIVATIVES OF 6,11-BICYCLOLIDES

RELATED APPLICATION

This application claims the benefit of U.S. Provisional Application No. 61/051,991, filed on May 9, 2008. The entire teachings of the above application are incorporated herein by reference.

TECHNICAL FIELD

The present invention relates to novel semisynthetic macrolides having antibacterial activity that are useful in the treatment and prevention of bacterial infections. More particularly, the invention relates to $sp^3$ C9 oxygenated compounds, compositions containing such compounds and methods for using the same, as well as processes for making such compounds.

BACKGROUND OF THE INVENTION

The spectrum of activity of macrolides, including erythromycin, covers most relevant bacterial species responsible for upper and lower respiratory tract infections. 14-membered ring macrolides are well known for their overall efficacy, safety and lack of serious side effects. Erythromycin, however, is quickly degraded into inactive products in the acidic medium of the stomach resulting in low bioavailability and gastrointestinal side effects. Improvement of erythromycin pharmacokinetics has been achieved through the synthesis of more acid-stable derivatives, for example, roxithromycin, clarithromycin, and the 15-membered ring macrolide azithromycin. However, all of these drugs, including 16-membered ring macrolides, present several drawbacks. They are inactive against $MLS_B$-resistant streptococci ($MLS_B$=Macrolides-Lincosamides-type B Streptogramines) and with the exception of azithromycin, weakly active against *Haemophilus influenzae*. Furthermore, the resistance of *Streptococcus pneumoniae* to erythromycin has increased significantly in recent years (5% to above 40%). There is high percentage of cross-resistance to penicillin among these isolates, with a worldwide epidemic spread of 10-40% in some areas.

Kashimura et al. have disclosed 6-O-methylerythromycin derivatives having a tricyclic basic nuclear structure in European Application 559896, published in Nov. 11, 1991. Also, Asaka et al. have disclosed 5-O-desoaminylerythronolide derivatives containing a tricyclic carbamate structure in PCT Application WO 93/21200, published Apr. 22, 1992.

Erythromycin derivatives containing a variety of substituents at the 6-O position have been disclosed in U.S. Pat. Nos. 5,866,549 and 6,075,011 as well as PCT Application WO 00/78773. Furthermore, Ma et al. have described erythromycin derivatives with aryl groups tethered to the C-6 position (Ma et al., *J. Med Chem.*, 44, pp 4137-4156 (2001)). PCT application WO 97/10251, published Mar. 20, 1997, discloses intermediates useful for preparation of 6-O-methyl 3-descladinose erythromycin derivatives. U.S. Pat. Nos. 5,866,549, 6,075,011, 6,878,691, 7,064,100 and PCT application WO 00/78773, published Dec. 28, 2000, also disclose certain 6-O-substituted erythromycin derivatives.

SUMMARY OF THE INVENTION

The present invention provides a novel class of $sp^3$ C-9 oxygenated compounds that possess superior antibacterial activity, particularly against *Haemophilus influenzae*. The present invention further provides a new synthetic route that would allow incorporation of an $sp^3$ oxygenated C-9 on a 6,11 bridged system.

The compounds of the present invention are represented by formula (I) as illustrated below:

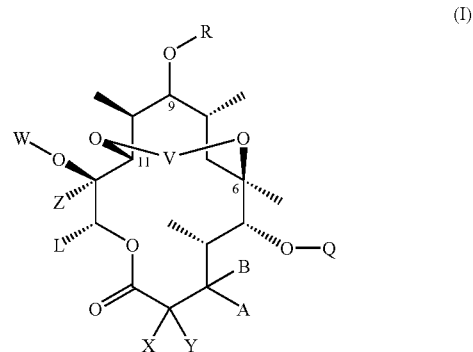

(I)

or a racemate, enantiomer, diastereomer, geometric isomer, tautomer, solvate, pharmaceutically acceptable salt, ester and prodrug thereof, wherein V is selected from the group consisting of:

(a) —$R_1$—, where $R_1$ is substituted or unsubstituted —$C_1$-$C_8$ alkylene-, —$C_2$-$C_8$ alkenylene- or —$C_2$-$C_8$ alkynylene- each containing 0, 1, 2, or 3 heteroatoms selected from O, S or N;

(b) —$R_1$—(C=O)—$R_2$—, where $R_2$ is independently selected from $R_1$;

(c) —$R_1$—(C=N-E-$R_3$)—$R_2$—, where E is absent, O, NH, NH(C=O), NH(C=O)NH or $NHSO_2$; where $R_3$ is independently selected from the group consisting of:
  (i) hydrogen;
  (ii) aryl; substituted aryl; heteroaryl; substituted heteroaryl;
  (iii) —$R_4$, where $R_4$ is substituted or unsubstituted —$C_1$-$C_8$ alkyl, —$C_2$-$C_8$ alkenyl or —$C_2$-$C_8$ alkynyl each containing 0, 1, 2, or 3 heteroatoms selected from O, S or N; and
  (iv) —$R_5$, where $R_5$ is substituted or unsubstituted —$C_3$-$C_{12}$ cycloalkyl each containing 0, 1, 2, or 3 heteroatoms selected from O, S or N;

(d) —$R_1$—(C=CH-J-$R_6$)—$R_2$—; where J is absent, O, CO, $SO_2$, NH, NH(C=O), NH(C=O)NH or $NHSO_2$; and wherein $R_6$ is independently selected from halogen and $R_3$;

(e) —$R_1$—[C(O$R_7$)(O$R_8$)]—$R_2$—, where $R_7$ and $R_8$ are selected from the group consisting of $C_1$-$C_{12}$ alkyl, aryl or substituted aryl; or $R_7$ and $R_8$ taken together are —(C$R_a R_b$)$_r$—, where r is 2 or 3; and each $R_a$ and $R_b$ is independently selected from hydrogen, aryl, and $R_4$; or (f) —$R_1$—[C(S$R_7$)(S$R_8$)]—$R_2$—;

R is selected from the group consisting of:
  (a) —$R_3$;
  (b) —C(O)$R_3$;
  (c) —C(O)O$R_3$;
  (d) —S(O)$_2 R_3$;
  (e) hydroxy prodrug group;
  (f) hydroxy protecting group; and
  (g) —C(O)N($R_9 R_{10}$); where $R_9$ and $R_{10}$ are each independently selected from $R_3$; alternatively, $R_9$ and $R_{10}$ taken together with the nitrogen atom to which they are connected form a substituted or unsubstituted 3- to 10-membered ring which may optionally contain one or more heterofunctions selected from the group consisting of: —O—, —N(R$_3$)—, —S(O)$_n$—, wherein n=0, 1 or 2;

W is selected from:
(a) hydrogen;
(b) hydroxy prodrug group;
(c) —R$_4$;
(d) —C(O)R$_3$;
(e) —C(O)O—R$_3$; and
(f) —C(O)N(R$_9$R$_{10}$);

one of A and B is R$_{11}$ and the other is OR$_{11}$, wherein R$_{11}$ is independently selected from:
(a) hydrogen;
(b) —R$_4$;
(c) —C(O)R$_3$;
(d) —C(O)NHR$_3$;
(e) —S(O)$_2$R$_3$;
(f) -monosaccharide; and
(g) -disaccharide;

alternatively, A and B are taken together with the carbon atom to which they are attached to form:
(a) C=O; or
(b) C=CH-J-R$_6$;

L is independently selected from R$_4$;

Q is:
(a) —R$_3$;
(b) —(C=O)R$_3$;
(c) —(C=O)NHR$_3$;
(d) —(C=O)OR$_3$;
(e) —S(O)$_2$R$_3$;
(f) monosaccharide;
(g) disaccharide; or
(h) trisaccharide;

Z is:
(a) hydrogen;
(b) —N$_3$;
(c) —CN;
(d) —NO$_2$;
(e) —CONH$_2$;
(f) —COOH;
(g) —CHO;
(h) —R$_4$;
(i) —COOR$_4$;
(j) —(C=O)R$_4$; or
(k) —(C=O)NR$_9$R$_{10}$; and each of X and Y is independently:
a) hydrogen;
b) hydroxy;
c) halogen; or
d) —R$_4$.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating bacterial infections in a subject in need of such treatment with said pharmaceutical compositions. Suitable carriers and formulations of the compounds of the present invention are disclosed.

DETAILED DESCRIPTION OF THE INVENTION

In a first embodiment of the compounds of the present invention are compounds represented by formula I as illustrated above, or a pharmaceutically acceptable salt, ester or prodrug thereof.

In one embodiment of the compounds of the present invention are compounds represented by formula II as illustrated below, or a pharmaceutically acceptable salt, ester or prodrug thereof:

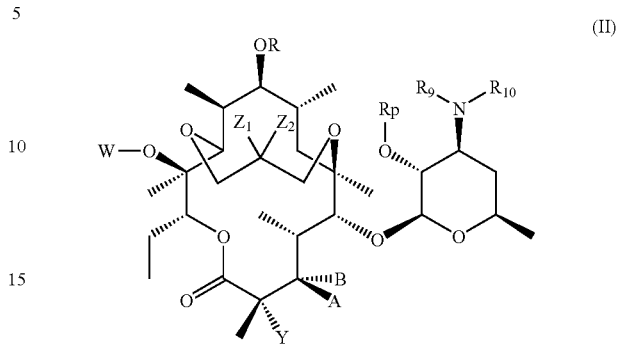

(II)

where Z$_1$ and Z$_2$ are independently selected from:
(a) hydrogen;
(b) deuterium;
(c) halogen;
(d) —R$_3$, where R$_3$ is independently selected from the group consisting of:
 (i) hydrogen;
 (ii) aryl; substituted aryl; heteroaryl; substituted heteroaryl; and
 (iii) —R$_4$, where R$_4$ is substituted or unsubstituted —C$_1$-C$_6$ alkyl, —C$_2$-C$_6$ alkenyl, or —C$_2$-C$_6$ alkynyl each containing 0, 1, 2, or 3 heteroatoms selected from O, S or N; and
 (iv) —R$_5$, where R$_5$ is substituted and unsubstituted —C$_3$-C$_{12}$ cycloalkyl each containing 0, 1, 2, or 3 heteroatoms selected from O, S or N;
(e) —C(O)-J$_1$-R$_3$, wherein J$_1$ is absent, O, or S and R$_3$ is as previously defined;
(f) —OR$_3$;
(g) —O(C=O)R$_3$;
(h) —O(C=O)OR$_3$;
(i) —O(C=O)NHR$_3$;
(j) —NH(C=O)R$_3$;
(k) —NH(C=O)NHR$_3$;
(l) —NH(C=O)OR$_3$;
(m) —NH(SO$_2$)R$_3$;
(n) —NH(SO$_2$)NHR$_3$;
(o) —NR$_9$R$_{10}$, where R$_9$ and R$_{10}$ are each independently selected from R$_3$; alternatively, R$_9$ and R$_{10}$ taken together with the nitrogen atom to which they are connected form a 3- to 10-membered ring which may optionally contain one or more heterofunctions selected from the group consisting of: —O—, —N(R$_3$)—, —S(O)$_n$—, wherein n=0, 1 or 2; and
(p) —C(O)—NR$_9$R$_{10}$;

alternatively, Z$_1$ and Z$_2$ taken together with the carbon atom to which they are attached are:
(a) C=O;
(b) C(OR$_7$)(OR$_8$), where R$_7$ and R$_8$ are selected from the group consisting of C$_1$-C$_{12}$ alkyl, aryl or substituted aryl; or R$_7$ and R$_8$ taken together is —(CR$_a$R$_b$)$_r$—, where r is 2 or 3; R$_a$ and R$_b$ are independently selected from hydrogen, aryl, and R$_4$;
(c) C(SR$_7$)(SR$_8$);
(d) C=CHR$_3$, where R$_3$ is as previously defined; or
(e) C=N-E-R$_3$, where E is absent, O, NH, NH(C=O), NH(C=O)NH or NHSO$_2$;

R$_p$ is hydrogen, hydroxy protecting group, ester or hydroxy prodrug group; A, B, R, W, Y, R$_9$, and R$_{10}$ are as previously defined.

In one embodiment of the compounds of the present invention are compounds represented by formula III as illustrated below, or a pharmaceutically acceptable salt, ester or prodrug thereof:

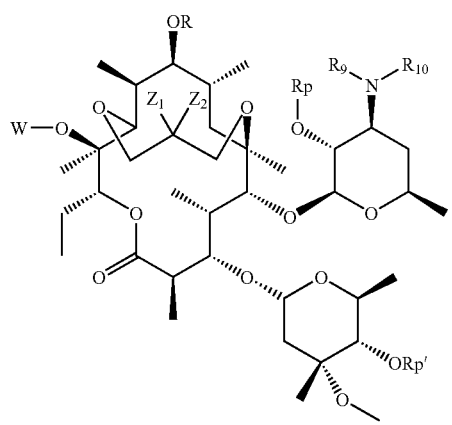

(III)

where R, W, $Z_1$, $Z_2$, $R_p$, $R_9$ and $R_{10}$ are as previously defined.

In one embodiment of the compounds of the present invention are compounds represented by formula IV as illustrated below, or a pharmaceutically acceptable salt, ester or prodrug thereof:

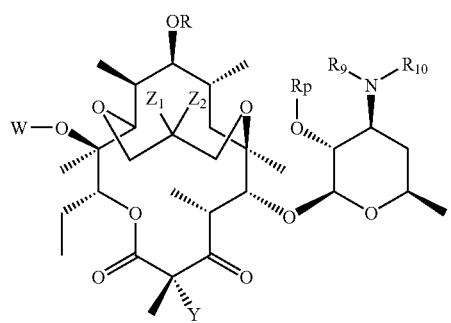

(IV)

where R, W, Y, $Z_1$, $Z_2$, $R_p$, $R_9$ and $R_{10}$ are as previously defined.

In one embodiment of the compounds of the present invention are compounds represented by formula V as illustrated below, or a pharmaceutically acceptable salt, ester or prodrug thereof:

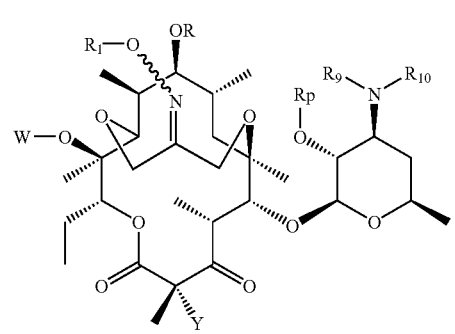

(V)

where W, R, Y, $R_p$, $R_3$, $R_9$ and $R_{10}$ are as previously defined.

In one embodiment of the compounds of the present invention are compounds represented by formula VI as illustrated below, or a pharmaceutically acceptable salt, ester or prodrug thereof:

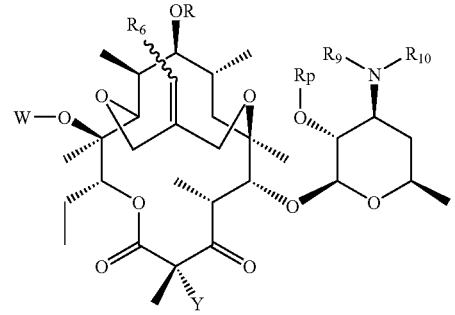

(VI)

where W, R, Y, $R_p$, $R_6$, $R_9$ and $R_{10}$ are as previously defined.

Representative compounds according to the invention are those selected from the group consisting of compounds (1)-(28) of the formula A:

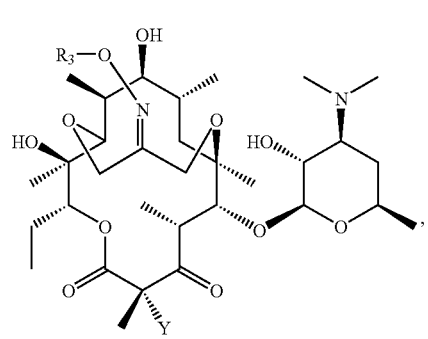

(A)

where for each compound $R_3$ and Y are set forth in Table 1.

TABLE 1

| Compound No. | Y | —$R_3$ |
|---|---|---|
| (1) | H | pyrazole-pyridine group |
| (2) | H | $H_2N$-thiadiazole-pyridine group |

TABLE 1-continued
| Compound No. | Y | —R₃ |
|---|---|---|
| (3) | H | 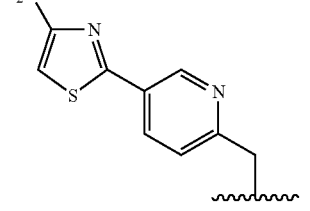 |
| (4) | H | 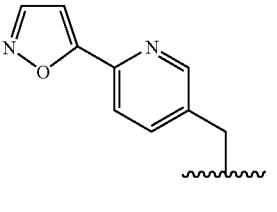 [SMILES: *Cc1ccc(-c2ccno2)nc1] |
| (5) | H | 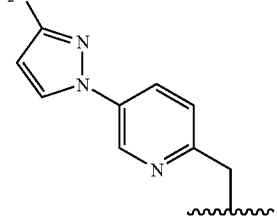 |
| (6) | H | 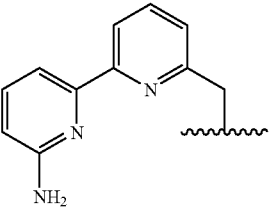 [SMILES: *Cc1cccc(-c2cccc(N)n2)n1] |
| (7) | H | 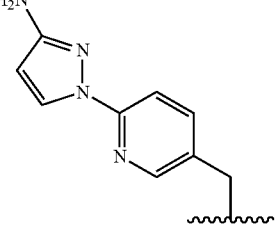 |
| (8) | H | 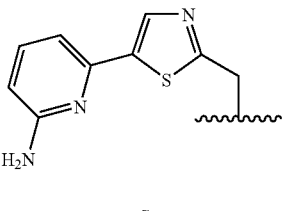 |
| (9) | H | 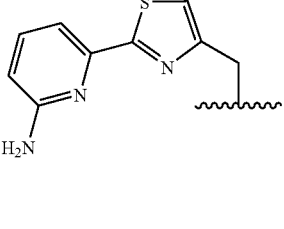 |
| (10) | F | 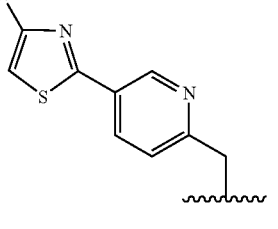 |
| (11) | F | 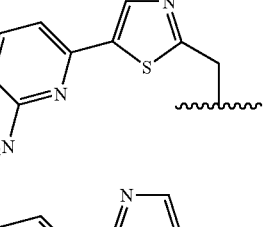 |
| (12) | F | 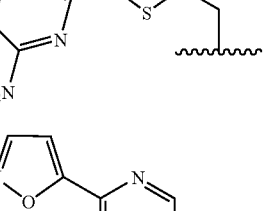 |
| (13) | F | 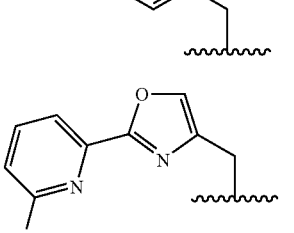 |
| (14) | F | 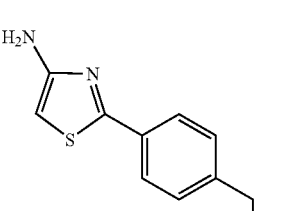 |
| (15) | F | 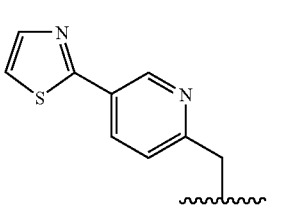 [SMILES: *Cc1ccc(-c2nccs2)cn1] |
| (16) | F | 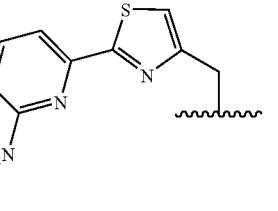 |
| (17) | F |  |

TABLE 1-continued

| Compound No. | Y | —R₃ |
|---|---|---|
| (18) | F | 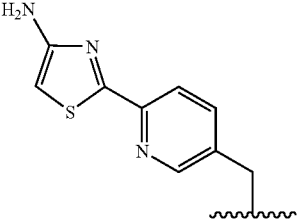 [SMILES: *Cc1ccc(-c2nc(N)cs2)nc1] |
| (19) | H | 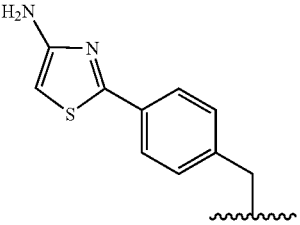 [SMILES: *Cc1ccc(-c2nc(N)cs2)cc1] |
| (20) | H | 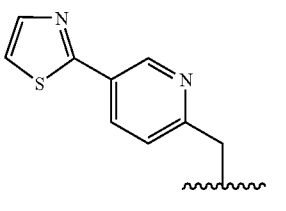 [SMILES: *Cc1ccc(-c2nccs2)cn1] |
| (21) | F | 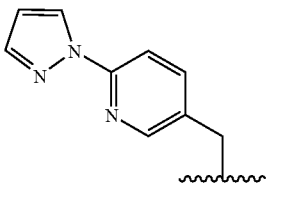 [SMILES: *Cc1ccc(-n2cccn2)nc1] |
| (22) | F | 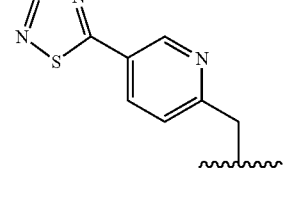 |
| (23) | F | 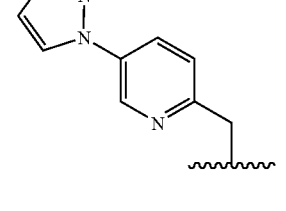 |
| (24) | F | 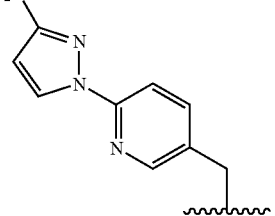 |
| (25) | F | 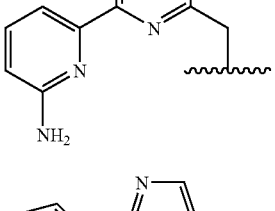 |
| (26) | H | 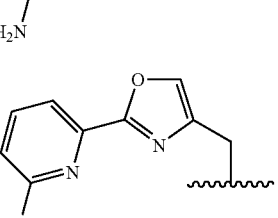 |
| (27) | H | 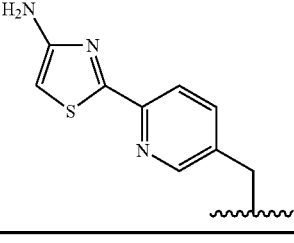 |
| (28) | H | 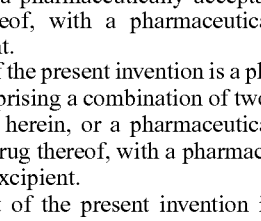 |

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art (such as penicillin, amoxicillin, azithromycin, erythromycin, ciprofloxacin, telithromycin, cethromycin, and the like), or a pharmaceutically acceptable salt, ester, or prodrug thereof, with a pharmaceutically acceptable carrier or excipient.

In addition, the present invention contemplates processes of making any compound delineated herein via any synthetic method delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms "$C_1$-$C_6$ alkyl,", "$C_1$-$C_8$ alkyl," or "$C_1$-$C_{12}$ alkyl," as used herein, refer to saturated, straight- or branched-chain hydrocarbon radicals containing from one to six, one to eight, or one to twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals.

The terms "$C_2$-$C_6$ alkenyl" or "$C_2$-$C_8$ alkenyl," as used herein, refer to straight- or branched-chain hydrocarbon radicals containing from two to six or from two to eight carbon atoms, respectively, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_6$ alkynyl" or "$C_2$-$C_8$ alkynyl," as used herein, refer to straight- or branched-chain hydrocarbon radicals containing from two to six or from two to eight carbon atoms, respectively, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_3$-$C_{12}$-cycloalkyl," as used herein, refers to a monocyclic or polycyclic saturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1]heptyl, and bicyclo [2.2.2] octyl.

The term "$C_3$-$C_8$ cycloalkenyl", or "$C_3$-$C_{12}$ cycloalkenyl" as used herein, refers to monocyclic or polycyclic carbocyclic ring compound having at least one carbon-carbon double bond. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a group derived from a monocyclic or bicyclic saturated carbocyclic ring compound. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —$NO_2$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$— heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "monosaccharide" embraces radicals of cladinose, allose, altrose, arabinose, erythrose, erythrulose, fructose, D-fucitol, L-fucitol, fucosamine, fucose, galactosamine, D-galactosaminitol, galactose, glucosamine, glucosaminitol, glucose, glyceraldehyde, glycerol, glycerone, gulose, idose, lyxose, mannosamine, annose, psicose, quinovose, quinovosamine, rhamnitol, rhamnosamine, rhamnose, ribose, ribulose, sorbose, tagatose, tartaric acid, threose, xylose and xylulose. The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, preferably galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine. It is understood that the monosaccharide and the like can be further substituted.

The terms "disaccharide", "trisaccharide" and "polysaccharide" embrace radicals of abequose, amicetose, amylose, apiose, arcanose, ascarylose, ascorbic acid, boivinose, cellobiose, cellotriose, chacotriose, chalcose, colitose, cymarose, 2-deoxyribose, 2-deoxyglucose, diginose, digitalose, digitoxose, evalose, evemitrose, gentianose, gentiobiose, hamamelose, inulin, isolevoglucosenone, isomaltose, isomaltotriose, isopanose, kojibiose, lactose, lactosamine, lactosediamine, laminarabiose, levoglucosan, levoglucosenone, β-maltose, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose, umbelliferose and the like. Further, it is understood that the "disaccharide", "trisaccharide" and "polysaccharide" and the like can be further substituted. Disaccharide also includes amino sugars and their derivatives, particularly, a mycaminose derivatized at the C-4' position or a 4 deoxy-3-amino-glucose derivatized at the C-6' position.

The term "trisaccharide" includes amino sugars and halo sugars, where halo sugars is saccharide group having at least one halogen substituent.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)$CH_3$), benzoyl (Bz or —C(O)$C_6H_5$), and trimethylsilyl (TMS or —Si($CH_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethane-sulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991);

Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of the invention, for example hydrates.

This invention also encompasses pharmaceutical compositions containing, and methods of treating bacterial infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, meningitis, sinusitus, bronchitis, tonsillitis, cystic fibrosis (CF) and mastoiditis related to infection by *Streptococcus pneumoniae, Haemophilus influenzae, Moraxella catarrhalis, Staphylococcus aureus, Peptostreptococcus* spp, or *Pseudomonas* spp.; pharyngitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C-F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae*; toxin diseases related to infection by *S. aureus* (food poisoning and Toxic shock syndrome), or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium acne*; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica, P. multocida, Mycoplasma bovis*, or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae, P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate broth medium for the observed bacterial isolates. Antimicrobial agents are serially diluted (2-fold) in DMSO to produce a concentration range from about 64 µg/ml to about 0.03 µg/ml. The diluted compounds (2 µl/well) are then transferred into sterile, uninoculated medium (0.2 mL) by use of a 96 fixed tip-pipetting station. The inoculum for each bacterial strain is standardized to approximately $5 \times 10^5$ CFU/mL by optical comparison to a 0.5 McFarland turbidity standard. The plates are inoculated with 10 µl/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 µg/ml to about 0.03 µg/ml.

All in vitro testing follows the guidelines described in the Approved Standards M7-A7 protocol, published by the Clinical Laboratory Standards Institute (CLSI).

The invention further provides compositions and methods of treating patients suffering from an inflammatory condition comprising administering to a patient in need thereof, a therapeutically effective amount of at least one compound of the invention. Specific examples of inflammatory conditions treatable according to the invention include, but are not limited to, scleritis; epi-scleritis; allergic conjunctivitis; pulmonary inflammatory diseases, particularly cystic fibrosis (CF), asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those patients susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention a compound according to any one of compounds of the invention, is administered to a patient in need of treatment for CF, in amount sufficient to prevent, diminish or eradicate symptoms of CF including chronic pulmonary inflammation and infection.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, bacterial infections, cystic fibrosis and inflammatory conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may appear in the following synthetic schemes and examples are:

Ac for acetyl;
AcOH for acetic acid;
AIBN for azobisisobutyronitrile;
BSA for N,O-bis(trimethysilyl)acetamide;
BINAP for 2,2'-bis(diphenylphosphino)-1,1'-binaphthyl;
$Boc_2O$ for di-tert-butyl-dicarbonate;
Boc for t-butoxycarbonyl;
Bpoc for 1-methyl-1-(4-biphenylyl)ethyl carbonyl;
Bz for benzoyl;
Bn for benzyl;
BocNHOH for tert-butyl N-hydroxycarbamate;
t-BuOK for potassium tert-butoxide;
$Bu_3SnH$ for tributyltin hydride;
BOP for (benzotriazol-1-yloxy)tris(dimethylamino)phosphonium Hexafluorophosphate;
Brine for sodium chloride solution in water;
CDI for carbonyldiimidazole;
$CH_2Cl_2$ for dichloromethane;
$CH_3$ for methyl;
$CH_3CN$ for acetonitrile;
$Cs_2CO_3$ for cesium carbonate;
CuCl for copper (I) chloride;
CuI for copper (I) iodide;
dba for dibenzylidene acetone;
dppb for diphenylphosphino butane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or $(i-Pr)_2EtN$ for N,N,-diisopropylethyl amine;
Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
$Et_2O$ for diethyl ether;
HATU for O-(7-azabenzotriazol-1-yl)-N,N,N',N',-tetramethyluronium Hexafluorophosphate;
HCl for hydrogen chloride;
HOBT for 1-hydroxybenzotriazole;
$K_2CO_3$ for potassium carbonate;
n-BuLi for n-butyl lithium;
i-BuLi for i-butyl lithium;
t-BuLi for t-butyl lithium;
PhLi for phenyl lithium;
LDA for lithium diisopropylamide;
TMEDA for N,N,N',N'-tetramethylethylenediamine;
LiTMP for lithium 2,2,6,6-tetramethylpiperidinate;
MeOH for methanol;
Mg for magnesium;
MOM for methoxymethyl;
Ms for mesyl or $-SO_2-CH_3$;
$Ms_2O$ for methanesulfonic anhydride or mesyl-anhydride;
$NaN(TMS)_2$ for sodium bis(trimethylsilyl)amide;
NaCl for sodium chloride;
NaH for sodium hydride;
$NaHCO_3$ for sodium bicarbonate or sodium hydrogen carbonate;
$Na_2CO_3$ sodium carbonate;
NaOH for sodium hydroxide;
$Na_2SO_4$ for sodium sulfate;
$NaHSO_3$ for sodium bisulfite or sodium hydrogen sulfite;
$Na_2S_2O_3$ for sodium thiosulfate;
$NH_2NH_2$ for hydrazine;
$NH_4HCO_3$ for ammonium bicarbonate;
$NH_4Cl$ for ammonium chloride;
NMMO for N-methylmorpholine N-oxide;
$NaIO_4$ for sodium periodate;
Ni for nickel;
OH for hydroxyl;
$OsO_4$ for osmium tetroxide;
TIPS for triisopropylsilyl;
TEA or $Et_3N$ for triethylamine;
TFA for trifluoroacetic acid;
THF for tetrahydrofuran;
TMS for trimethylsilyl;
TPP or $PPh_3$ for triphenylphosphine;
Troc for 2,2,2-trichloroethyl carbonyl;
Ts for tosyl or $-SO_2-C_6H_4-CH_3$;
$Ts_2O$ for tolylsulfonic anhydride or tosyl-anhydride;
TsOH for p-tolylsulfonic acid;
Pd for palladium;
Ph for phenyl;
POPd for dihydrogen dichlorobis(di-tert-butylphosphinito-κP)palladate(II);
$Pd_2(dba)_3$ for tris(dibenzylideneacetone) dipalladium (0);
$Pd(PPh_3)_4$ for tetrakis(triphenylphosphine)palladium (0);
$PdCl_2(Ph_3P)_2$ for trans-dichlorobis(triphenylphosphine) palladium (II);
Pt for platinum;
Rh for rhodium;
Ru for ruthenium;
TBS for tert-butyl dimethylsilyl; or
TMS for trimethylsilyl;
TMSCl for trimethylsilyl chloride.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims. The intermediates of the present invention can be prepared by methods which are known in the art such as processes described by U.S. Pat. Nos. 5,892,008, 6,878,691 and 6,753,318, each of which is incorporated herein by reference in its entirety.

Surprisingly, when the 6,11 bridge system is already incorporated into the species and intermediates disclosed in U.S. Pat. Nos. 6,878,691 and 6,753,318, reduction of the ketone to the corresponding hydroxy moiety cannot be achieved by any known methods. While not bound by theory, it is believed that the 6,11 bridge system has changed the conformation and/or blocked the C9 position of the molecule thereby preventing reduction at that position. The present invention provides a new synthetic route that would allow incorporation of an $sp^3$ oxygenated C-9 and a 6,11-bridged system thereby providing compounds with superior antibiotic activity, particularly against *Haemophilus influenzae*.

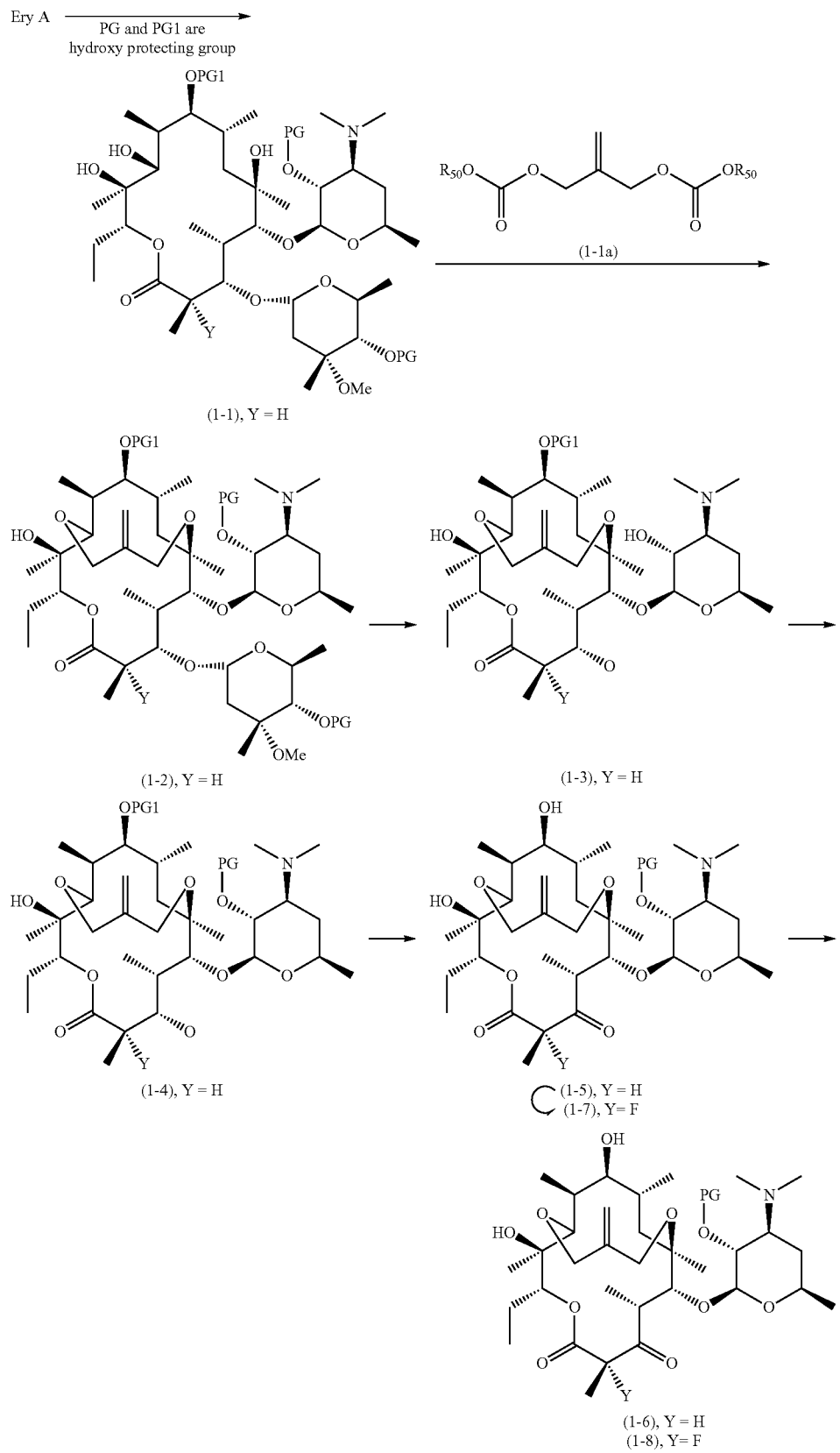

Scheme 1 describes one method of preparing intermediates 1-6, which are key intermediates for preparing compounds of the invention. Commercially available erythromycin A can be converted to intermediate (1-1) by the methods disclosed in U.S. Pat. No. 5,892,008. Formation of the 6,11-bridge can be achieved by reacting with a compound of formula (1-1) with a suitable alkylating agent of the formula (1-1a):

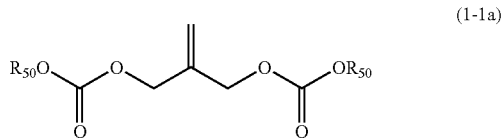

(1-1a)

wherein $R_{50}$ is —$C_1$-$C_{12}$ alkyl, —$C_2$-$C_{12}$ alkenyl, or —$C_2$-$C_{12}$ alkynyl optionally substituted with one or more substitutents selected from halogen, aryl, substituted aryl, heteroaryl, or substituted heteroaryl; —$C_3$-$C_{12}$ cycloalkyl.

Most palladium (0) catalysts are expected to work in this process. Some palladium (II) catalysts, such as palladium (II) acetate, which is converted into a palladium (0) species in-situ by the actions of a phosphine, will work as well. See, for example, Beller et al. *Angew. Chem. Int. Ed. Engl.*, 1995, 34 (17), 1848. The palladium catalyst can be selected from, but not limited to, palladium (II) acetate, tetrakis(triphenylphosphine)palladium(0), tris(dibenzylideneacetone)dipalladium, tetradibenzylideneacetone)dipalladium and the like. Palladium on carbon and palladium (II) halide catalysts are less preferred than other palladium catalysts for this process. Phosphines suitable for this process include, but are not limited to triphenylphosphine, bis(diphenylphosphino)methane, bis(diphenylphosphino)ethane, bis(diphenylphosphino)propane, 1,4-bis(diphenylphosphino)butane, bis(diphenylphosphino)pentane, and tri-o-tolyl-phosphine, and the like. The reaction is carried out in an aprotic solvent, preferably at elevated temperature, preferably at or above 50° C. Suitable aprotic solvents include, but are not limited to, tetrahydrofuran, N,N-dimethylformamide, dimethyl sulfoxide, N-methyl-2-pyrrolidone, toluene, hexamethylphosphoric triamide, 1,2-dimethoxyethane, methyl-tert-butyl ether, heptane, acetonitrile, isopropyl acetate and ethyl acetate. Generally, the alkylating agents have the formula (1-1a) as previously described. The preferred alkylating agents are those wherein $R_{50}$ is tert-butyl, isopropyl or isobutyl. The alkylating reagents are prepared by reaction of a diol with a wide variety of compounds for incorporating the di-carbonate moiety. These compounds include, but are not limited to, tert-butyl chloroformate, di-tert-butyl dicarbonate, and 1-(tert-butoxycarbonyl)imidazole and the reaction is carried out in the presence of an organic or an inorganic base.

Removal of the cladinose moiety of the macrolide (1-2) either by mild acid hydrolysis or by enzymatic hydrolysis to afford compound (1-3). Representative acids include, but are not limited to, dilute hydrochloric acid, sulfuric acid, perchloric acid, chloroacetic acid, dichloroacetic acid or trifluoroacetic acid. Suitable solvents for the reaction include, but are not limited to, methanol, ethanol, isopropanol, butanol, water and mixtures there of.

Conversion of compounds of formula (1-3) to compounds of formula (1-4) can be accomplished by oxidation of the 3-hydroxy group to a 3-oxo group using Dess-Martin periodinane (for further details concerning the Dess-Martin oxidation see D. B. Dess, J. C. Martin, *J. Org. Chem.* 48, 4155 (1983)), a Corey-Kim reaction with N-chlorosuccinimide-dimethylsulfide (for further details concerning the Corey-Kim oxidation reaction see E. J. Corey, C. U. Kim, *J. Am. Chem. Soc.* 94, 7586 (1972), or a Moffat oxidation with a carbodiimide-DMSO complex in the presence of pyridinium trifluoroacetate, TPAP, PDC, and the like (for further details concerning the Moffat oxidation see J. G. Moffatt, "Sulfoxide-Carbodiimide and Related Oxidations" in *Oxidation* vol. 2, R. L. Augustine, D. J. Trecker, Eds. (Dekker, New York, 1971) pp 1-64; T. T. Tidwell, *Org. React.* 39, 297-572 passim (1990); and T. V. Lee, *Comp. Org. Syn.* 7, 291-303 passim (1991).

Selective deprotection of the C-9 hydroxy moiety of (1-4) to form compounds of formula (1-5) can be achieved by procedures known in the art such as described in T. W. Greene and P. G. M. Wuts, *Protective Groups in Organic Synthesis*, 3rd. Ed., John Wiley and Sons (1999).

The transformation of (1-5) to (1-7) can be achieved by treatment with a fluorinating agent. Fluorinating reagents include, but are not limited to N-fluorobenzenesulfonamide in presence of base, 10% $F_2$ in formic acid, 3,5-dichloro-1-fluoropyridinium triflate, $(CF_3SO_2)_2NF$, N-fluoro-N-methyl-p-toluenesulfonamide in presence of base, N-Fluoropyridinium triflate, and N-fluoroperfluoropiperidine in presence of base.

Suitable bases for the fluorinating reaction are alkali metal hydride bases, such as NaH and KH, or amine bases, such as LDA or triethylamine. The choice of base is dependent on the fluorinating agent but this is well known within the art.

Conversion of alkenes (1-5) or (1-7) into ketones (1-6) or (1-8) respectively, can be accomplished by ozonolysis followed by decomposition of the ozonide with the appropriate reducing agents. The reaction is typically carried out in an inert solvent such as, but not limited to, methanol, ethanol, ethyl acetate, glacial acetic acid, chloroform, methylene chloride or hexane or mixtures thereof, preferably methanol, preferably at −78° C. to −20° C. Representative reducing agents are, for example, triphenylphosphine, trimethylphosphite, thiourea, and dimethyl sulfide, preferably triphenylphosphine. A more thorough discussion of ozonolysis and conditions therefor may be found in J. March, *Advanced Organic Chemistry*, 4$^{th}$ ed., Wiley & Son, Inc, 1992. Alternatively, compounds of formula (1-6) can be prepared from compounds of formula (1-5) by dihydroxydation with $OsO_4$ followed by $NaIO_4$ cleavage.

Scheme 2

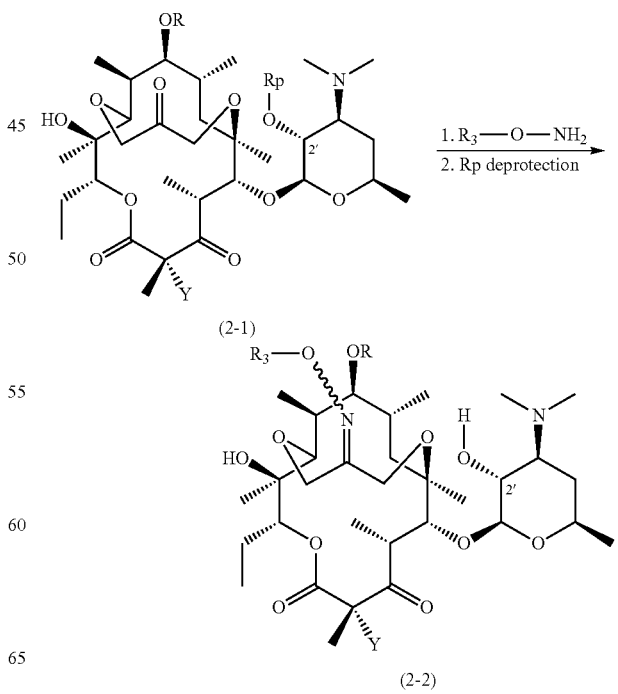

Scheme 2 outlines formation of oxime derivatives from key intermediate (2-1) followed by 2'-deprotection of Rp to yield compounds of the invention. Oxime formation can be carried out under mild acidic conditions, such as but not limited to, dilute hydrochloric acid, sulfuric acid, perchloric acid, chloroacetic acid, dichloroacetic acid or trifluoroacetic acid with commercially available hydroxylamines or hydroxylamines known in the art such as ones disclosed in U.S. Pat. No. 6,878,691 or hydroxylamines specifically prepared to improve antibacterial activity. Deprotection of the 2'-Rp protecting group can be carried achieved according to procedures known in the art such as described in T. W. Greene and P. G. M. Wuts, *Protective Groups in Organic Synthesis*, 3rd. Ed., John Wiley and Sons (1999).

lamine under either acidic or basic conditions in a variety of solvents. Representative acids include, but are not limited to, hydrochloric, phosphoric, sulfuric, p-toluenesulfonic, and pyridinium p-toluene sulfonate. Likewise, representative bases include, but are not limited to, triethylamine, pyridine, diisopropylethyl amine, 2,6-lutidine, and the like. Appropriate solvents include, but are not limited to, methanol, ethanol, water, tetrahydrofuran, 1,2-dimethoxyethane, and ethyl acetate or combination thereof. Preferably the reaction is carried out in ethanol with acids such as hydrochloric acid, methanesulfonic acid, perchloric acid and the like.

It will be appreciated by one skilled in the art that ketones of formula (3-0) can be transformed into alkenes of formula (3-2) and (3-7) via Wittig reaction with the appropriate phos-

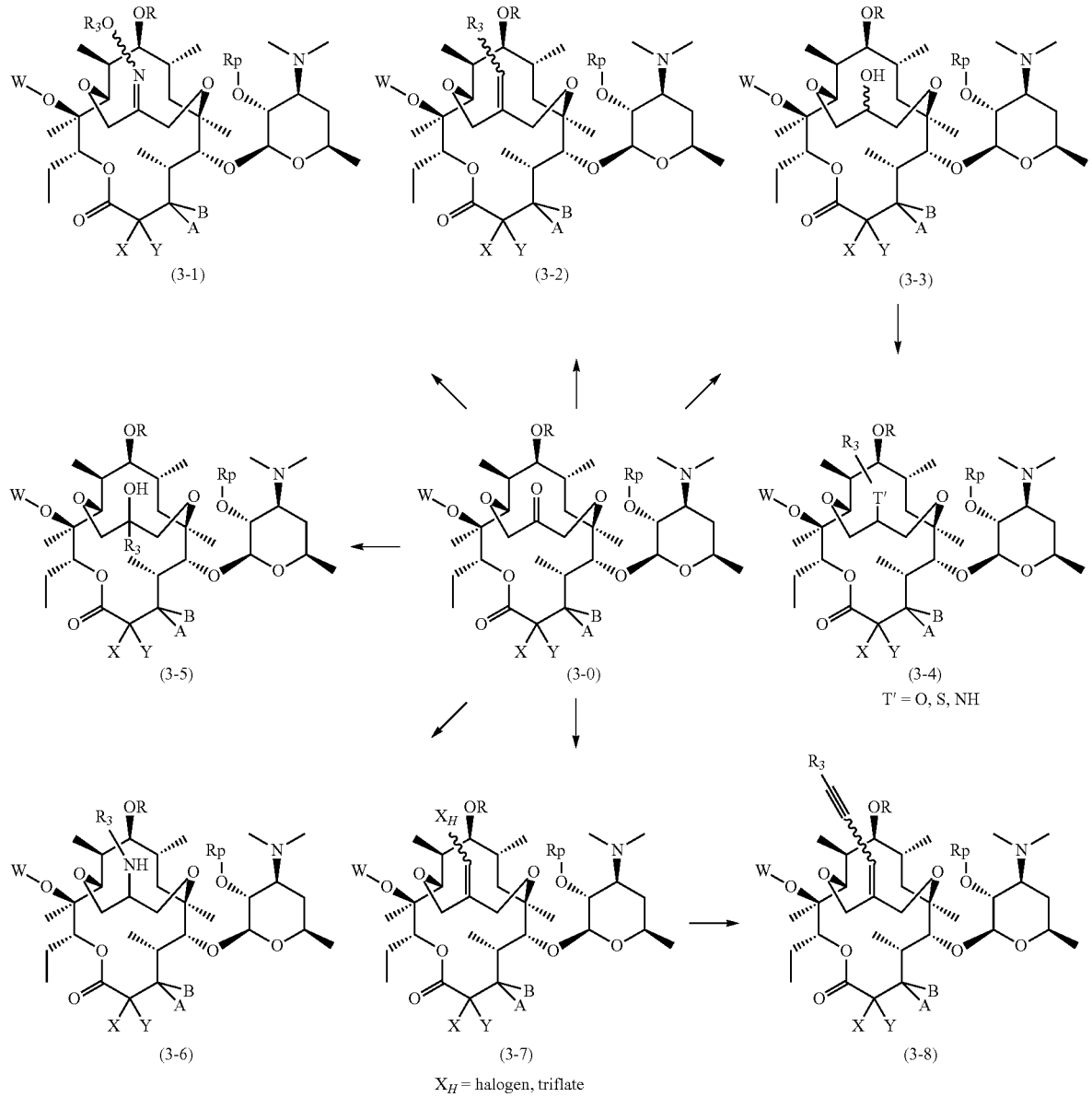

Compounds according to the invention of the formula (3-0) can be further functionalized in a variety of ways. Scheme 3 details a procedure for the conversion of the ketone of formula (3-0) into an oxime of formula (3-1). Oxime formation can be accomplished using the appropriate substituted hydroxyphonium salt in the presence of a base, see (a) Burke, *Tetrahedron Lett.*, 1987, 4143-4146, (b) Rathke and Nowak, *J. Org. Chem.*, 1985, 2624-2626, (c) Maryanoff and Reitz, *Chem. Rev.*, 1989, 863-927. Furthermore, vinyl halides of formula (3-7) can be functionalized by Sonogashira coupling with alkynes in the presence of a palladium catalyst, a copper halide and an amine base to give compounds of formula (3-8) (see (a) Sonogashira, *Comprehensive Organic Synthesis*, Volume 3, Chapters 2,4; (b) Sonogashira, *Synthesis* 1977, 777.). In a similar manner, alkenes of formula (3-2) can be obtained from vinyl halides (3-7) via Suzuki cross coupling with organoboron reagents in the presence of a palladium catalyst and a base, or via Stille cross coupling with organostananes in the presence of a palladium catalyst (see (a) Suzuki, *J. Organomet. Chem.* 1999, 576, 147-168, (b) Stille, *Angew. Chem. Int. Ed. Engl.*, 1986, 508-524 (c) Farina, *J. Am. Chem. Soc.*, 1991, 9585-9595).

Furthermore, alcohols of type (3-3) can be prepared by reduction of the corresponding ketone of formula (3-0) under a variety of conditions (see Hudlicky, M. *Reductions in Organic Chemistry*, Ellis Horwood Limited: Chichester, 1984). The alcohols thus derived can be further modified to give compounds of formula (3-4). A process to generate compounds of formula (3-4) includes, but is not limited to, alkylation of the alcohol with an electrophile or conversion of the alcohol into a leaving group, such as a triflate, tosylate, phosphonate, halide, or the like, followed by displacement with a heteroatom nucleophile (e.g. an amine, alkoxide, sulfide or the like).

Yet another means by which to functionalize ketones of formula (3-0) is via addition of Grignard reagents to form alcohols of formula (3-5). The requisite Grignard reagents are readily available via the reaction of a variety of alkyl or aryl halides with magnesium under standard conditions (see B. S. Furniss, A. J. Hannaford, P. W. G Smith, A. R. Tatchell, *Vogel's Textbook of Practical Organic Chemistry*, 5$^{th}$ ed., Longman, 1989). The addition is performed in an inert solvent, generally at low temperatures. Suitable solvents include, but are not limited to, tetrahydrofuran, diethylether, 1,4-dioxane, 1,2-dimethoxyethane, and hexanes. Preferably the solvent is tetrahydrofuran or diethylether. Preferably the reaction is run at −78° C. to 0° C.

In a similar way, reaction with other organometallic reagents gives rise to alcohols of formula (3-5). Examples of useful organometallic reagents include, but are not limited to, organo-aluminum, organo-lithium, organo-cerium, organozinc, organo-thallium, and organo-boron reagents. A more thorough discussion of organometallic reagents can be found in B. S. Furniss, A. J. Hannaford, P. W. G Smith, A. R. Tatchell, *Vogel's Textbook of Practical Organic Chemistry* 5$^{th}$ ed., Longman, 1989.

Ketone of formula (3-0) can be further utilized by conversion into amine of formula (3-6) via a reductive amination. Reductive amination is achieved by treating the ketone with an amine in the presence of a reducing agent to obtain the product amine (3-6). The reaction can be carried out either with or without added acid. Examples of acids that are commonly used include, but are not limited to, hydrochloric, phosphoric, sulfuric, acetic, and the like. Reducing agents that effect reductive amination include, but are not limited to, hydrogen and a catalyst, zinc and hydrochloric acid, sodium cyanoborohydride, sodium borohydride, iron pentacarbonyl, and alcoholic potassium hydroxide. Generally alcoholic solvents are used. The preferred conditions use sodium cyanoborohydride in methanol with added acetic acid.

It will be appreciated by one skilled in the art, that the unsaturated compounds represented by compounds (3-2) and (3-8) can be reduced to form the corresponding saturated compound (see Hudlicky, M., *Reductions in Organic Chemistry*, Ellis Horwood Limited Chichester, 1984).

Scheme 4

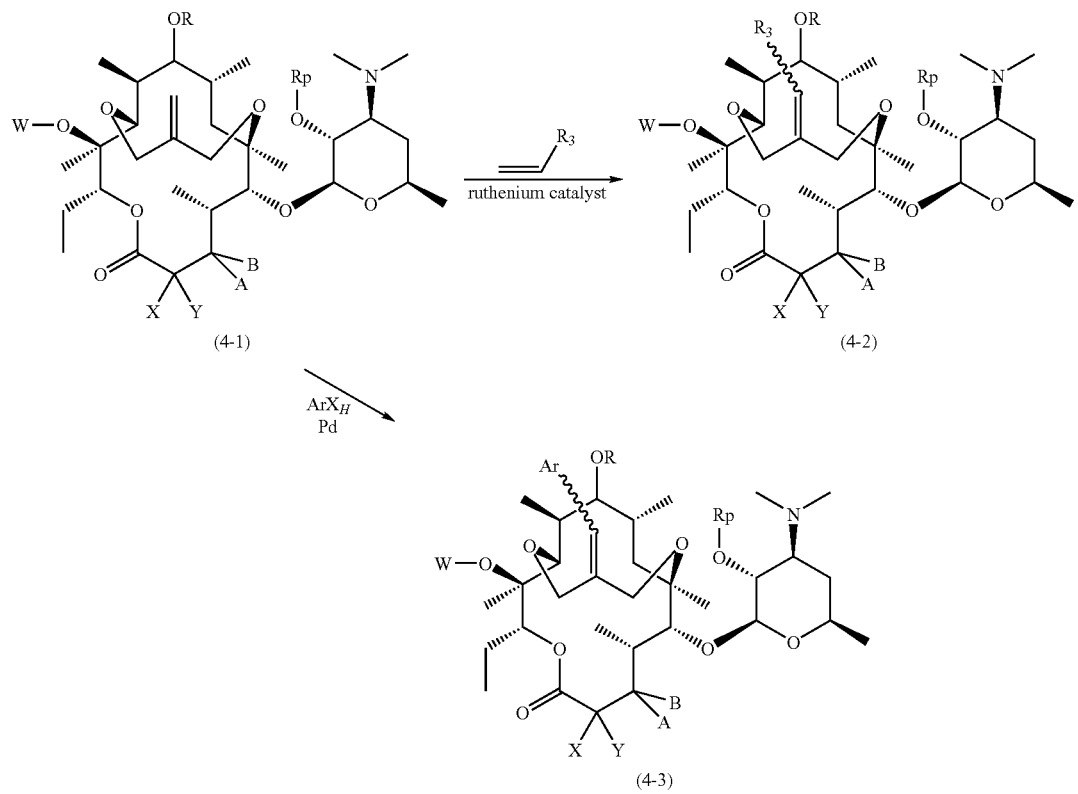

Compounds of the invention according to formula (4-1) are also capable of further functionalization to generate compounds of the present invention. Alkene (4-1) can be treated with an aryl halide or aryl triflate in the presence of a palladium catalyst [Pd(0) or Pd(II)] to provide compound (4-3): (See (a) Heck, *Palladium Reagents in Organic Synthesis*, Academic Press: New York, 1985, Chapter 1; (b) Sonogashira, *Comprehensive Organic Synthesis*, Volume 3, Chapters 2,4; (c) Sonogashira, *Synthesis* 1977, 777). Under the Heck coupling conditions, regioisomers and stereoisomers of the double bond are possible. Alternatively, compound (4-1) can undergo a cross metathesis reaction with vinylaromatic derivatives using ruthenium catalysts to give compounds of formula (4-2) (see (a) *J. Org. Chem.* 2000, 65, 2204-2207; (b) Reviews: *Synlett.* 1999, 2, 267; (c) Reviews: Ivin, K. J.; Mol, J. C., *Olefin Metathesis and Metathesis Polymerization*, 2$^{nd}$ ed., Academic Press: New York, 1997; (d) *J. Org. Chem.* 1999, 64, 4798-4816; (e) *Angew. Chem., Int. Ed. Engl.* 1997, 36, 2036-2056; (f) *Tetrahedron* 1998, 54, 4413-4450).

Scheme 5

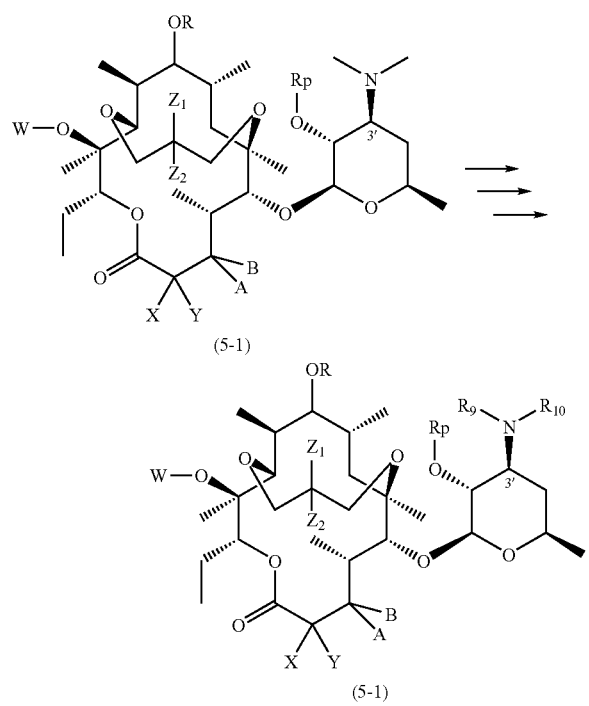

(5-1)

It will be appreciated that compounds of the present invention include modification of the 3' N of compounds of the formula (5-1). Compounds of formula (5-2) can be made via the methods known in the art, such as in U.S. Pat. Nos. 6,034,069 and 6,387,885.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula A, Wherein R$_3$ is

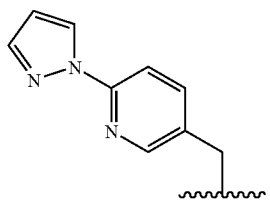 [SMILES: *Cc1ccc(-n2cccn2)nc1]

and Y=H (Compound 1)

Step 1a: Compound 1-1, where PG1 is TIPS and PG is TMS, (24 g, 23.1 mmol) was placed with 1-1a, where R$_{50}$ is t-butyl, (14 g, 48.6 mmol), 1,4-bis(diphenylphosphino)butane (1.5 g, 3.5 mmol) and tris(dibenzylidine acetone)dipalladium (2.11 g, 2.3 mmol) in THF (125 mL) and heated at reflux for 1 h. The reaction was cooled, quenched with water, extracted with ethyl acetate, dried (MgSO$_4$) and concentrated to a dark foam that was used in the next step. MS: (ESI) m/z (M+H): 1088.66.

Step 1b: Compound from step 1a was placed with ethyl alcohol (100 mL) and 2M aqueous HCl (35 mL) and heated at 90° C. for 30 min. The reaction was cooled, quenched with 3N aqueous NaOH, extracted with ethyl acetate, dried (MgSO$_4$) and concentrated to a dark foam that was used in the next step. MS: (ESI) m/z (M+H): 786.66.

Step 1c: Acetic anhydride (3.3 mL, 35 mmol) was added to a room temperature solution of Compound from step 1b in DCM (115 mL) and stirred for 2 h. Dess Martin Periodinane (20 g, 47 mmol) was added to this reaction mixture and stirred for 4 h. The reaction was quenched with sodium thiosulfate and saturated sodium bicarbonate, extracted with DCM, dried (MgSO$_4$) and concentrated to a dark foam that was used in the next step. MS: (ESI) m/z (M+H): 826.64.

Step 1d: Concentrated HCl (215 mL) was added dropwise to a solution of compound from step 1c in THF (150 mL) at 0° C. The reaction was warmed to rt over 2 h, quenched with 3N aqueous NaOH/ice, extracted with ethyl acetate, dried (MgSO$_4$), concentrated and purified by flash chromatography to obtain the title compound as a yellow foam. MS: (ESI) m/z (M+H): 670.46. $^{13}$C NMR (CDCl$_3$): δ 205.16, 169.81, 168.46, 143.41, 122.12, 101.48, 82.63, 80.28, 79.09, 77.70, 76.71, 74.82, 71.77, 71.21, 69.28, 65.01, 63.55, 51.54, 48.14, 42.00, 40.81, 37.65, 31.07, 30.70, 23.76, 21.51, 21.17, 20.93, 20.64, 17.28, 15.82, 14.08, 12.43.

Step 1e: Ozone gas was bubbled through a solution of compound from step 1d (11.2 mmol) and camphor sulfonic acid (2.85 g, 12.3 mmol) in DCM (50 mL) and MeOH (30 mL) maintained at −78° C. till the reaction was complete by MS. Dimethyl sulfide (7.8 mL, 112 mmol) was added to the reaction mixture and warmed to room temperature over 4 h. The reaction was quenched with saturated, aqueous NaHCO$_3$, extracted with ethyl acetate, dried (MgSO$_4$) and concentrated to a yellow foam that was used in the oxime forming step. MS: (ESI) m/z (M+H): 672.39.

Step 1f: A solution of Compound from step 1e (0.035 g, 0.05 mmol) in THF was added to a slurry of O-(6-Pyrazol-1-yl-pyridin-3-ylmethyl)-hydroxylamine (0.050 g, 0.26 mmol) in 2N HCl maintained at 0° C., followed by the addition of water to effect a clear solution. The reaction was warmed to room temperature over 30 min, quenched with saturated aqueous NaHCO$_3$, extracted with ethyl acetate, dried (MgSO$_4$), concentrated and suspended in MeOH overnight. The solvents were removed in vacuo and the residue purified on RP-HPLC to afford the titled compound and its corresponding Z-isomer. Data for E isomer: MS: (ESI) m/z (M+H): 802.32. $^{13}$C NMR (CDCl$_3$): δ 204.9, 168.84, 155.84, 151.56, 148.47, 142.34, 139.58, 130.96, 127.35, 112.34, 108.05, 103.77, 82.33, 81.93, 81.27, 78.9, 76.88, 76.72, 76.01, 73.49, 70.46, 69.31, 66.56, 63.76, 63.0, 51.94, 48.82, 40.64, 29.99, 23.75, 21.56, 21.32, 20.97, 17.25, 16.47, 14.53, 12.34.

Example 2

Compound of Formula A, Wherein R$_3$ is

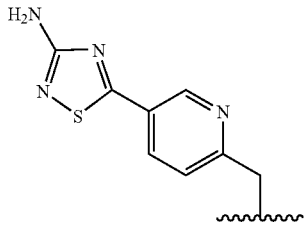

and Y=H (Compound 2)

The E and Z isomers of the titled compound were prepared using the procedure of Example 1, step 1f substituting O—[5-(3-Amino-[1,2,4]thiadiazol-5-yl)-pyridin-2-ylmethyl]-hydroxylamine for O-(6-Pyrazol-1-yl-pyridin-3-ylmethyl)-hydroxylamine. Data for E isomer: MS: (ESI) m/z (M+H): 835.13. $^{13}$C NMR (CDCl$_3$): δ 204.77, 184.38, 170.0, 168.61, 161.3, 156.25, 147.3, 134.65, 125.47, 121.85, 103.87, 81.99, 81.72, 80.55, 78.51, 76.43, 76.26, 76.15, 70.3, 69.47, 65.79, 63.44, 62.4, 51.62, 48.60, 40.19, 30.72, 29.63, 28.18, 23.45, 21.23, 21.09, 20.81, 17.08, 16.2, 14.2, 12.00.

Example 3

Compound of Formula A, Wherein R$_3$ is

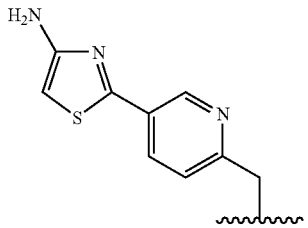

and Y=H (Compound 3)

The E and Z isomers of the titled compound were prepared using the procedure of Example 1, step 1f substituting O-[5-(4-Amino-thiazol-2-yl)-pyridin-2-ylmethyl]-hydroxylamine for O-(6-Pyrazol-1-yl-pyridin-3-ylmethyl)-hydroxylamine. Data for E isomer: MS: (ESI) m/z (M+H): 834.43. $^{13}$C NMR (CDCl$_3$): δ 204.85, 168.84, 162.52, 159.12, 157.53, 156.15, 146.74, 133.85, 128.76, 121.97, 103.42, 91.24, 82.15, 81.97, 81.02, 78.83, 76.68, 76.63, 76.27, 70.23, 68.93, 66.49, 63.79, 62.75, 51.88, 48.68, 40.59, 29.9, 23.68, 21.49, 21.15, 21.02, 17.28, 16.48, 14.52, 12.2.

Example 4

Compound of Formula A, Wherein R$_3$ is

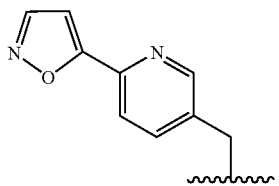

and Y=H (Compound 4)

The E and Z isomers of the titled compound were prepared using the procedure of Example 1, step 1f substituting O-(6-Isoxazol-5-yl-pyridin-3-ylmethyl)-hydroxylamine for O-(6-Pyrazol-1-yl-pyridin-3-ylmethyl)-hydroxylamine. Data for E isomer: MS: (ESI) m/z (M+H): 803.45. $^{13}$C NMR (CDCl$_3$): δ 204.88, 168.84, 168.67, 155.96, 151.23, 150.12, 145.99, 137.32, 134.28, 120.76, 104.16, 101.66, 82.24, 81.60, 80.95, 78.68, 76.67, 75.76, 73.30, 69.73, 65.98, 63.53, 62.75, 51.79, 48.89, 40.41, 28.33, 23.62, 21.43, 21.33, 20.73, 17.07, 16.37, 14.34, 12.28.

Example 5

Compound of Formula A, Wherein R$_3$ is

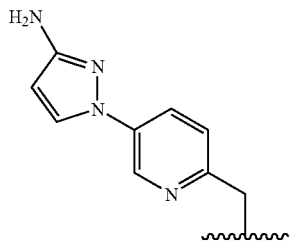 [SMILES: *Cc1ccc(-n2ccc(N)n2)cn1]

and Y=H (Compound 5)

The E and Z isomers of the titled compound were prepared using the procedure of Example 1, step 1f substituting O-[5-(3-Amino-pyrazol-1-yl)-pyridin-2-ylmethyl]-hydroxylamine for O-(6-Pyrazol-1-yl-pyridin-3-ylmethyl)-hydroxylamine. Data for E isomer: MS: (ESI) m/z (M+H): 817.59. $^{13}$C NMR (CDCl$_3$): δ 204.94, 168.88, 156.57, 156.12, 154.25, 138.71, 135.77, 128.03, 125.62, 122.62, 104.13, 97.29, 82.31, 82.03, 81.08, 78.77, 76.60, 76.25, 70.54, 69.68, 66.03, 63.79, 62.76, 51.87, 48.81, 40.39, 28.47, 23.66, 21.53, 21.34, 21.11, 17.24, 16.42, 14.46, 12.18.

Example 6

Compound of Formula A, Wherein $R_3$ is

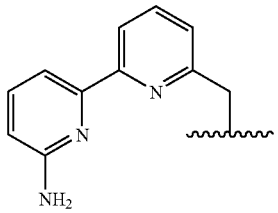 [SMILES: *Cc1cccc(-c2cccc(N)n2)n1]

and Y=H (Compound 6)

The E and Z isomers of the titled compound were prepared using the procedure of Example 1, step 1f substituting O-(6'-Amino-[2,2']bipyridinyl-6-ylmethyl)-hydroxylamine for O-(6-Pyrazol-1-yl-pyridin-3-ylmethyl)-hydroxylamine. Data for E isomer: MS: (ESI) m/z (M+H): 828.68.

Example 7

Compound of Formula A, Wherein $R_3$ is

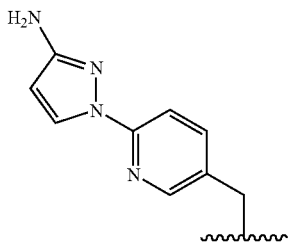 [SMILES: *Cc1ccc(-n2ccc(N)n2)nc1]

and Y=H (Compound 7)

The E and Z isomers of the titled compound were prepared using the procedure of Example 1, step 1f substituting O-[6-(3-Amino-pyrazol-1-yl)-pyridin-3-ylmethyl]-hydroxylamine for O-(6-Pyrazol-1-yl-pyridin-3-ylmethyl)-hydroxylamine. Data for E isomer: MS: (ESI) m/z (M+H): 817.51.

Example 8

Compound of Formula A, Wherein $R_3$ is

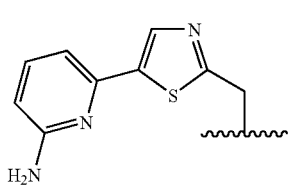 [SMILES: *Cc1ncc(-c2cccc(N)n2)s1]

and Y=H (Compound 8)

The E and Z isomers of the titled compound were prepared using the procedure of Example 1, step 1f substituting O-[5-(6-Amino-pyridin-2-yl)-thiazol-2-ylmethyl]-hydroxylamine for O-(6-Pyrazol-1-yl-pyridin-3-ylmethyl)-hydroxylamine. Data for E isomer: Data for E isomer: MS: (ESI) m/z (M+H): 834.46.

Example 9

Compound of Formula A, Wherein $R^3$ is

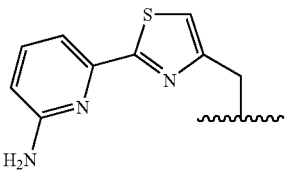

and Y=H (Compound 9)

The E and Z isomers of the titled compound were prepared using the procedure of Example 1, step 1f substituting O-[2-(6-Amino-pyridin-2-yl)-thiazol-4-ylmethyl]-hydroxylamine for O-(6-Pyrazol-1-yl-pyridin-3-ylmethyl)-hydroxylamine. Data for E isomer: MS: (ESI) m/z (M+H): 834.51. $^{13}$C NMR (CDCl$_3$): δ C13(CDCl3, Selected) 205.1, 169.8, 168.8, 158.3, 155.6, 154.3, 149.7, 138.3, 119.2, 110.5, 110.0, 104.2, 82.3, 81.9, 81.2, 78.8, 76.7, 76.0, 72.3, 70.6, 69.8, 66.1, 63.7, 62.9, 51.9, 48.9, 41.9, 40.5, 38.7, 30.6, 28.5, 23.7, 21.6, 21.4, 20.9, 17.2, 16.6, 14.5, 12.3, 11.7.

Example 10

Compound of Formula A, Wherein $R_3$ is

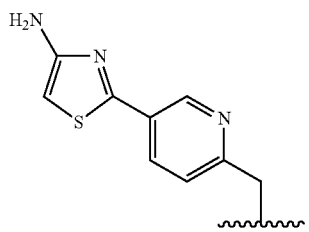

and Y=F (Compound 10)

Step 10a: To a solution of compound from step 1d in DMF and t-BuOH at −10° C. was added KO$^t$Bu and stirred for 1 hour followed by the addition of N-fluorbenzenesulfonimide and continued to stirred at −10° C. for 30 minutes. The reaction was quenched by the addition of ethyl vinyl ether, warmed to room temperature, quenched by the addition of saturated sodium bicarbonate, extracted with ethyl acetate, dried (MgSO$_4$), concentrated and purified by flash chromatography to afford a white foam.

Step 10b: Ozonolysis on this substrate was carried out in a similar manner as described for Example 1, Step 1e substituting Compound from Step 10a for Compound for Step 1d. This product from Step 10b was used in the oxime forming step.

Step 10c: The E and Z isomers of the titled compound were prepared using the procedure of Example 1, step 1f substituting O-[5-(4-Amino-thiazol-2-yl)-pyridin-2-ylmethyl]-hydroxylamine for O-(6-Pyrazol-1-yl-pyridin-3-ylmethyl)-hydroxylamine. Data for E isomer: MS: (ESI) m/z (M+H): 852.67.

Example 11

Compound of Formula A, Wherein $R_3$ is

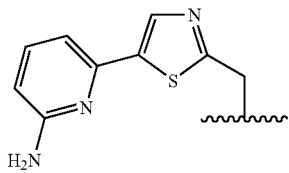

and Y=F (Compound 11)

The E and Z isomers of the titled compound were prepared using the procedure of Example 1, step 1f substituting O-[5-(6-Amino-pyridin-2-yl)-thiazol-2-ylmethyl]-hydroxylamine for O-(6-Pyrazol-1-yl-pyridin-3-ylmethyl)-hydroxylamine. Data for E isomer: MS: (ESI) m/z (M+H): 852.34.

Example 12

Compound of Formula A, Wherein $R_3$ is

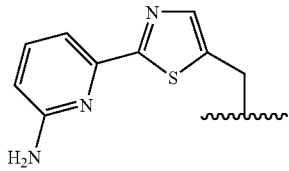 [SMILES: *Cc1cnc(-c2cccc(N)n2)s1]

and Y=F (Compound 12)

The E and Z isomers of the titled compound were prepared using the procedure of Example 1, step 1f substituting O-[2-(6-Amino-pyridin-2-yl)-thiazol-5-ylmethyl]-hydroxylamine for O-(6-Pyrazol-1-yl-pyridin-3-ylmethyl)-hydroxylamine. Data for E isomer: MS: (ESI) m/z (M+H): 852.17.

Example 13

Compound of Formula A, Wherein $R_3$ is

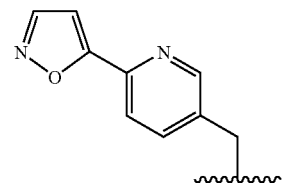 [SMILES: *Cc1ccc(-c2ccno2)nc1]

and Y=F (Compound 13)

The E and Z isomers of the titled compound were prepared using the procedure of Example 1, step 1f substituting O-(6-Isoxazol-5-yl-pyridin-3-ylmethyl)-hydroxylamine for O-(6-Pyrazol-1-yl-pyridin-3-ylmethyl)-hydroxylamine. Data for E isomer: MS: (ESI) m/z (M+H): 821.57. $^{13}$C NMR (CDCl$_3$): δ C13(CDCl3, Selected) 205.1, 204.9, 168.9, 165.9, 165.7, 155.4, 151.3, 150.1, 146.1, 137.3, 134.4, 120.8, 104.4, 101.7, 99.3, 97.6, 82.6, 81.8, 81.2, 79.7, 76.8, 75.3, 73.4, 70.6, 69.9, 66.0, 63.4, 61.9, 43.6, 40.8, 40.5, 29.7, 28.4, 25.5, 25.3, 23.3, 21.4, 20.0, 17.0, 15.5, 12.3, 10.5.

Example 14

Compound of Formula A, Wherein $R_3$ is

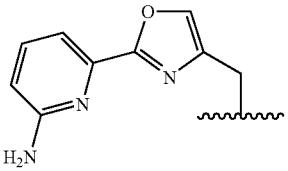

and Y=F (Compound 14)

The E and Z isomers of the titled compound were prepared using the procedure of Example 1, step 1f substituting O-[2-(6-Amino-pyridin-2-yl)-oxazol-4-ylmethyl]-hydroxylamine for O-(6-Pyrazol-1-yl-pyridin-3-ylmethyl)-hydroxylamine. Data for E isomer: MS: (ESI) m/z (M+H): 836.36.

Example 15

Compound of Formula A, wherein $R_3$ is

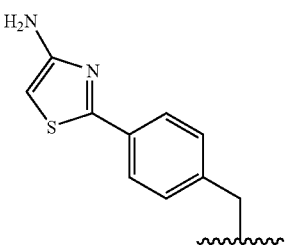

and Y=F (Compound 15)

The E and Z isomers of the titled compound were prepared using the procedure of Example 1, step 1f substituting O-[4-(4-Amino-thiazol-2-yl)-benzyl]-hydroxylamine for O-(6-Pyrazol-1-yl-pyridin-3-ylmethyl)-hydroxylamine. Data for E isomer: MS: (ESI) m/z (M+H): 851.34.

Example 16

Compound of Formula A, Wherein $R_3$ is

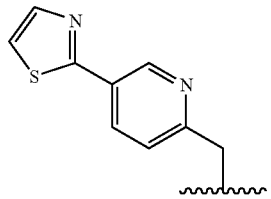 [SMILES: *Cc1ccc(-c2nccs2)cn1]

and Y=F (Compound 16)

The E and Z isomers of the titled compound were prepared using the procedure of Example 1, step 1f substituting O-(5-Thiazol-2-yl-pyridin-2-ylmethyl)-hydroxylamine for O-(6-Pyrazol-1-yl-pyridin-3-ylmethyl)-hydroxylamine. Data for E isomer: MS: (ESI) m/z (M+H): 837.31. $^{13}$C NMR (CDCl$_3$): δ C13(CDCl3, Selected) 205.0, 204.8, 166.0, 165.8, 165.2, 159.7, 155.7, 147.4, 144.3, 134.5, 128.7, 122.0, 119.7, 104.3, 99.3, 97.6, 82.6, 82.0, 81.5, 79.7, 76.7, 75.6, 70.6, 69.8, 66.1, 63.6, 61.9, 40.7, 40.5, 30.2, 28.5, 25.5, 25.4, 23.3, 21.4, 20.2, 17.1, 15.5, 12.4.

Example 17

Compound of Formula A, Wherein $R_3$ is

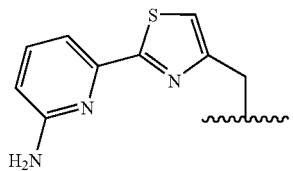

and Y=F (Compound 17)

The E and Z isomers of the titled compound were prepared using the procedure of Example 1, step 1f substituting O-[2-(6-Amino-pyridin-2-yl)-thiazol-4-ylmethyl]-hydroxylamine for O-(6-Pyrazol-1-yl-pyridin-3-ylmethyl)-hydroxylamine. Data for E isomer: MS: (ESI) m/z (M+H): 852.47.

Example 18

Compound of Formula A, Wherein $R_3$ is

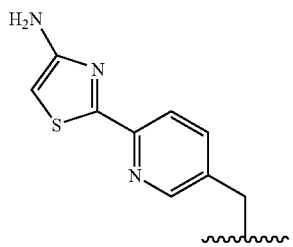 [SMILES: *Cc1ccc(-c2nc(N)cs2)nc1]

and Y=F (Compound 18)

The E and Z isomers of the titled compound were prepared using the procedure of Example 1, step 1f, substituting O-[6-(4-Amino-thiazol-2-yl)-pyridin-3-ylmethyl]-hydroxylamine for O-(6-Pyrazol-1-yl-pyridin-3-ylmethyl)-hydroxylamine. Data for E isomer: MS: (ESI) m/z (M+H): 852.17.

The hydroxylamines were prepared according to literature procedures and procedures disclosed in U.S. Pat. No. 6,878,691 and US Published Application No. 2009/0118506.

Representative Compounds with Improved Antibacterial Activities:

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate broth medium for the observed bacterial isolates. Antimicrobial agents are serially diluted (2-fold) in DMSO to produce a concentration range from about 64 μg/ml to about 0.03 μg/ml. The diluted compounds (2 μl/well) are then transferred into sterile, uninoculated medium (0.2 mL) by use of a 96 fixed tip-pipetting station. The inoculum for each bacterial strain is standardized to approximately 5×10$^5$ CFU/mL by optical comparison to a 0.5 McFarland turbidity standard. The plates are inoculated with 10 μl/well of adjusted bacterial inoculum. The 96 well plates are covered and incubated at 35+/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The compounds of the invention generally demonstrated an MIC in the range from about 64 μg/ml to about 0.03 μg/ml.

All in vitro testing follows the guidelines described in the Approved Standards M7-A7 protocol, published by the Clinical Laboratory Standards Institute (CLSI).

Table II below provides MIC data for compounds of the invention and related species from U.S. Pat. No. 6,878,691 and US Published Application No. 2009/0118506, each of which is incorporated herein by reference. The values in the table are minimum inhibition concentration (MIC) and are expressed as ug/mL.

TABLE II
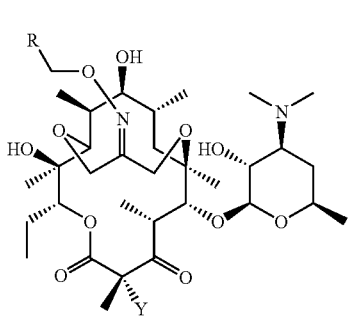
|  |  |  | H. influenzae MIC (µg/mL) | | | H. influenzae MIC (µg/mL) | |
| --- | --- | --- | --- | --- | --- | --- | --- |
| Compound # | R = Sidechain | Y | strain 33929 | strain 49247 | Z3 | strain 33929 | strain 49247 |
| 1 | 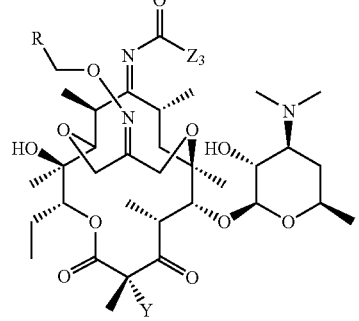 | H | 4 | 2 | Me | 4 | 8 |
| 2 | 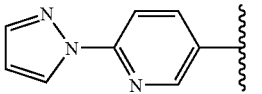 [SMILES: *c1ccc(-n2cccn2)nc1] | H | 1 | 1 | Me | 4 | 4 |
| 3 | 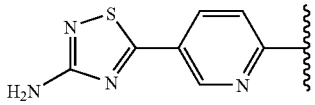 | H | 4 | 2 | Me | 4 | 4 |
| 4 | 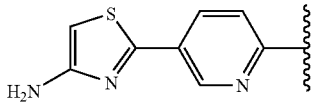 | H | 1 | 1 | Me | 4 | 4 |
| 5 | 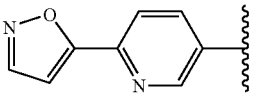 [SMILES: *c1ccc(-c2ccno2)nc1] | H | 2 | 2 | Me | 8 | 8 |
| 6 | 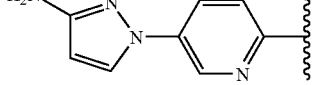 | H | 1 | 1 | Me | 8 | 4 |
| 7 | 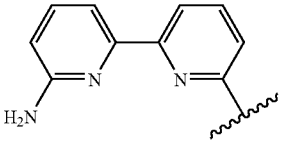 [SMILES: *c1cccc(-c2cccc(N)n2)n1] | H | 1 | 1 | Me | 8 | 8 |
| 8 | 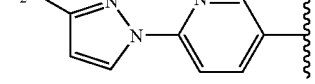 | H | 2 | 1 | Et | 4 | 4 |
| 9 | 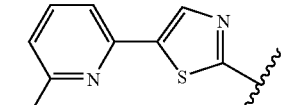 | H | 1 | 1 | Me | — | — |

TABLE II-continued

|  |  |  | H. influenzae MIC (μg/mL) | | | H. influenzae MIC (μg/mL) | |
| --- | --- | --- | --- | --- | --- | --- | --- |
| Compound # | R = Sidechain | Y | strain 33929 | strain 49247 | Z3 | strain 33929 | strain 49247 |
| 10 | 4-amino-thiazol-2-yl-(pyridin-5-yl) | F | 4 | 1 | Me | 4 | 2 |
| 11 | 6-amino-pyridin-2-yl-(thiazol-5-yl) | F | 1 | 1 | Me | 4 | 4 |
| 12 | 6-amino-pyridin-2-yl-(thiazol-2-yl) | F | 2 | 1 | Me | 2 | 2 |
| 13 | isoxazol-5-yl-(pyridin-5-yl) | F | 2 | 1 | Me | — | — |
| 14 | 6-amino-pyridin-2-yl-(oxazol-4-yl) | F | 2 | 1 | Me | 2 | 2 |
| 15 | 4-amino-thiazol-2-yl-(phenyl) | F | 4 | 4 | Et | 8 | 8 |
| 16 | thiazol-2-yl-(pyridin-5-yl) | F | 2 | — | Et | 4 | 4 |
| 17 | 6-amino-pyridin-2-yl-(thiazol-4-yl) | F | 1 | 1 | Me | 4 | — |
| 18 | 4-amino-thiazol-2-yl-(pyridin-5-yl) | F | 2 | 1 | Et | 8 | 8 |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Although the invention has been described with respect to various preferred embodiments, it is not intended to be limited thereto, but rather those skilled in the art will recognize that variations and modifications may be made therein which are within the spirit of the invention and the scope of the appended claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by formula (I):

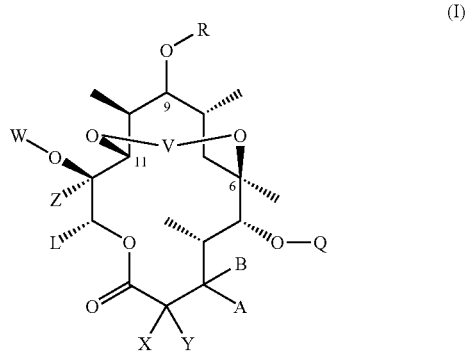

or a pharmaceutically acceptable salt or ester thereof,
wherein V is
—$R_1$—(C=N-E-$R_3$)—$R_2$—, where E is and $R_3$ is $C_1$-alkyl substituted with a monocyclic heteroaryl group or monocyclic aryl group wherein said monocyclic heteroaryl group or monocyclic aryl group is substituted with a substituted or unsubstituted monocyclic heteroaryl group R is
hydrogen;

W is selected from:
(a) hydrogen;
(b) hydroxy prodrug group;
(c) —$R_4$;
(d) —C(O)$R_{12}$;
(e) —C(O)O—$R_{12}$; and
(f) —C(O)N($R_9R_{10}$);

one of A and B is $R_{11}$ and the other is O$R_{11}$, wherein $R_{11}$ is independently selected from:
(a) hydrogen;
(b) —$R_4$;
(c) —C(O)$R_{12}$;
(d) —C(O)NH$R_{12}$;
(e) —S(O)$_2R_{12}$;
(f) monosaccharide; and
(g) —disaccharide;

alternatively, A and B are taken together with the carbon atom to which they are attached to form:
(a) C=O; or
(b) C=CH-J-$R_6$;

L is independently selected from $R_4$;

Q is:
(a) —$R_{12}$;
(b) —C(O)$R_{12}$;
(c) —C(O)NH$R_{12}$;
(d) —C(O)O$R_{12}$;
(e) —S(O)$_2R_{12}$;
(f) monosaccharide;
(g) disaccharide; or
(h) trisaccharide;

Z is:
(a) hydrogen;
(b) —$N_3$;
(c) —CN;
(d) —$NO_2$;
(e) —$CONH_2$;
(f) —COOH;
(g) —CHO;
(h) —$R_4$;
(i) —COO$R_4$;
(j) —(C=O)$R_4$; or
(k) —(C=O)N$R_9R_{10}$ each of X and Y is independently:
a) hydrogen;
b) hydroxy;
c) halogen; or
d) —$R_4$;

$R_1$ and $R_2$ are independently substituted or unsubstituted —$C_1$-$C_8$ alkylene, or —$C_2$-$C_8$ alkenylene—each containing 0, 1, 2, or 3 heteroatoms selected from O, S or N;

$R_4$ is substituted or unsubstituted —$C_1$-$C_8$ alkyl, —$C_2$-$C_8$ alkenyl or —$C_2$-$C_8$ alkenyl each containing 0, 1, 2, or 3 heteroatoms selected from O, S or N;

$R_5$ is substituted or unsubstituted —$C_3$-$C_{12}$ cycloalkyl each containing 0, 1, 2, or 3 heteroatoms selected from O, S or N;

$R_6$ is selected from halogen and $R_{12}$;

$R_9$ and $R_{10}$ are each independently selected from $R_{12}$; alternatively, $R_9$ and $R_{10}$ taken together with the nitrogen atom to which they are connected form a substituted or unsubstituted 3-to 10-membered ring which may optionally contain one or more heterofunctions selected from the group consisting of: —O—, —N($R_{12}$)—, —S(O)$_n$—, wherein n =0, 1 or 2; and $R_{12}$ is selected from the group consisting of:
(i) hydrogen;
(ii) aryl; substituted aryl; heteroaryl; substituted heteroaryl;
(iii) $R_4$; and
(iv) $R_5$.

2. A compound according to claim 1 represented by formula (II):

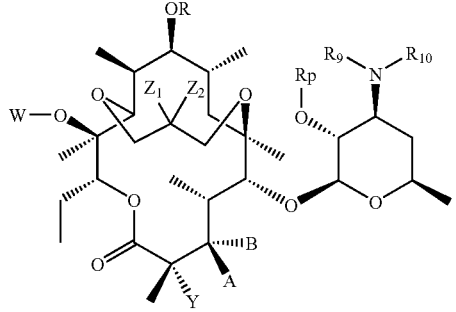

(II)

or a pharmaceutically acceptable salt or ester thereof, where
$Z_1$ and $Z_2$ taken together with the carbon atom to which they are attached form
C=N-E-$R_3$;
$R_p$ is hydrogen, or a hydroxy protecting group;
and A, B, W, Y, R, E, $R_3$, $R_9$, and $R_{10}$ are as defined in claim 1.

3. A compound according to claim 1 represented by formula (V):

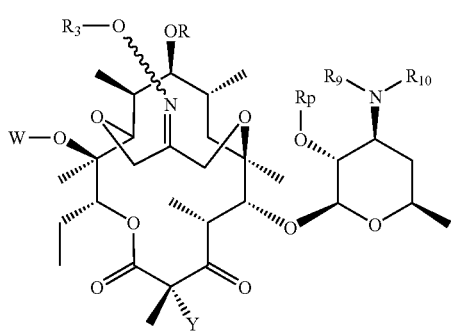

(V)

or a pharmaceutically acceptable salt or ester thereof, wherein $R_p$ is hydrogen or a hydroxy protecting group and W, R, Y, $R_3$, $R_9$ and $R_{10}$ are as defined in claim 1.

4. A compound of claim 1 having the Formula A, selected from compounds 1-28 of Table 1:

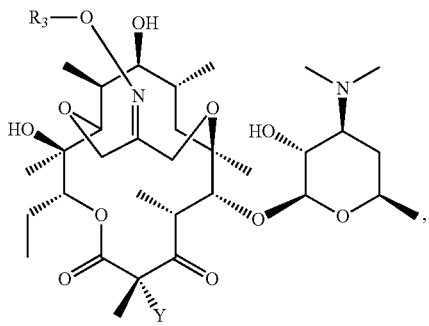

(A)

or a pharmaceutically acceptable salt or ester thereof, wherein Y and $R_3$ are delineated for each compound in Table 1:

TABLE 1

| Compound No. | Y | —$R_3$ |
|---|---|---|
| (1) | H | pyrazole-pyridine group |
| (2) | H | $H_2N$-thiadiazole-pyridine group |
| (3) | H | $H_2N$-thiazole-pyridine group |
| (4) | H | isoxazole-pyridine group |
| (5) | H | $H_2N$-pyrazole-pyridine group |
| (6) | H | bipyridine-$NH_2$ group |
| (7) | H | $H_2N$-pyrazole-pyridine group |

TABLE 1-continued

| Compound No. | Y | —R₃ |
|---|---|---|
| (8) | H | 6-amino-pyridin-2-yl-thiazol-2-yl-methyl (pyridine with NH₂, linked to thiazole at 5-position) |
| (9) | H | 6-amino-pyridin-2-yl-thiazol-2-yl (linked at thiazole 4-position) |
| (10) | F | 4-amino-thiazol-2-yl-pyridin-5-yl-methyl |
| (11) | F | 6-amino-pyridin-2-yl-thiazol-5-yl |
| (12) | F | 6-amino-pyridin-2-yl-thiazol-2-yl |
| (13) | F | isoxazol-5-yl-pyridin-2-yl |
| (14) | F | 6-amino-pyridin-2-yl-oxazol-2-yl |
| (15) | F | 4-amino-thiazol-2-yl-phenyl |
| (16) | F | thiazol-2-yl-pyridin-5-yl |
| (17) | F | 6-amino-pyridin-2-yl-thiazol-2-yl |
| (18) | F | 4-amino-thiazol-2-yl-pyridin-2-yl |
| (19) | H | 4-amino-thiazol-2-yl-phenyl |
| (20) | H | thiazol-2-yl-pyridin-5-yl |
| (21) | F | pyrazol-1-yl-pyridin-2-yl |
| (22) | F | 3-amino-1,2,4-thiadiazol-5-yl-pyridin-2-yl |

TABLE 1-continued

| Compound No. | Y | —R₃ |
|---|---|---|
| (23) | F | (3-amino-pyrazol-1-yl)pyridinylmethyl |
| (24) | F | (3-amino-pyrazol-1-yl)pyridinylmethyl (isomer) |
| (25) | F | (6-amino-bipyridinyl)methyl |
| (26) | H | (6-amino-pyridinyl-thiazolyl)methyl |
| (27) | H | (6-amino-pyridinyl-oxazolyl)methyl |
| (28) | H | (4-amino-thiazolyl-pyridinyl)methyl |

5. A pharmaceutical composition comprising a therapeutically effective amount of a compound of claim 1 or a pharmaceutically acceptable salt or ester thereof, in combination with a pharmaceutically acceptable carrier.

6. A method for treating a bacterial infection in a subject, comprising administering to said subject a therapeutically effective amount of a pharmaceutical composition according to claim 5.

7. A method of treating cystic fibrosis in subject, comprising administering to said subject, a therapeutically effective amount of a pharmaceutical composition of claim 5.

8. A t, therapeutically effective amount of a pharmaceutical composition of claim 5.

9. (Withdrawn/Currently Amended) A process for preparing a compound of claim 1, comprising the step of:

(a) reacting a compound represented by the formula

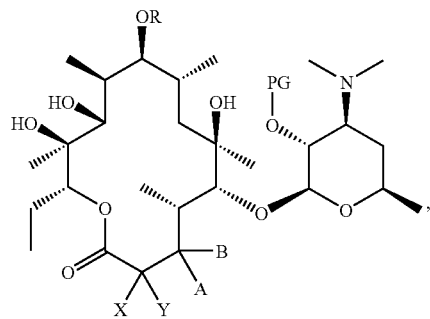

wherein A, B, X, and Y are as defined in claim 1 and R and PG are each a hydroxy protecting group, with an alkylating agent of formula

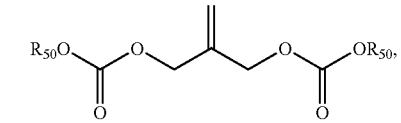

where $R_{50}$ is —$C_1$-$C_{12}$ alkyl, —$C_1$-$C_{12}$ alkenyl, or —$C_1$-$C_{12}$ alkynyl, in the presence of a palladium catalyst;

(b) oxidizing the double bond to the corresponding ketone;

(c) reacting the compound from step (b) with $R_3ONH_2$, where $R_3$ is defined in claim 1, in the presence of an acid or a base; and (d) optionally deprotecting the product of step (c).

* * * * *

UNITED STATES PATENT AND TRADEMARK OFFICE
CERTIFICATE OF CORRECTION

PATENT NO. : 8,383,785 B2
APPLICATION NO. : 12/437616
DATED : February 26, 2013
INVENTOR(S) : Rajesh Iyengar et al.

It is certified that error appears in the above-identified patent and that said Letters Patent is hereby corrected as shown below:

In the Claims:

At Column 49

In claim 1, at line 44, after the word is and before the word and, insert -- O --.

At Column 56

In claim 8, at line 13, delete "A t," and insert -- A method of treating inflammation in a subject comprising administering to said subject, -- and In claim 9, at line 15, delete "(Withdrawn/Currently Amended)".

Signed and Sealed this
Twenty-first Day of May, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,383,785 B2 | Page 1 of 1 |
| APPLICATION NO. | : 12/437616 | |
| DATED | : February 26, 2013 | |
| INVENTOR(S) | : Iyengar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 636 days.

Signed and Sealed this
Seventeenth Day of September, 2013

Teresa Stanek Rea
*Deputy Director of the United States Patent and Trademark Office*